United States Patent [19]

Cheng et al.

[11] Patent Number: 5,440,023
[45] Date of Patent: Aug. 8, 1995

[54] METHOD FOR MAKING VALPROIC ACID DERIVATIVES

[75] Inventors: Anthony K. Cheng, Brea; Thomas S. Dobashi, Rosemead, both of Calif.

[73] Assignee: Beckman Instruments, Inc., Fullerton, Calif.

[21] Appl. No.: 947,710

[22] Filed: Sep. 18, 1992

[51] Int. Cl.⁶ ............... C07K 17/00; G01N 33/531; C07C 55/00; C07C 227/00
[52] U.S. Cl. ............... 530/405; 530/362; 530/363; 530/367; 530/400; 530/403; 530/406; 436/543; 562/553; 562/590
[58] Field of Search .......... 562/553, 590; 530/367, 530/362, 603, 363, 400, 405, 406; 436/543; 435/188

[56] References Cited

U.S. PATENT DOCUMENTS

| | | |
|---|---|---|
| 2,971,024 | 2/1961 | Zaugg . |
| 4,238,389 | 12/1980 | Leung et al. ............ 435/7.9 |
| 4,261,974 | 4/1981 | Buckler et al. . |
| 4,443,366 | 4/1984 | Sunahara et al. . |
| 4,517,303 | 5/1985 | Freytag et al. ............ 436/501 |
| 4,786,594 | 11/1988 | Khanna et al. ............ 436/503 |
| 4,968,742 | 11/1990 | Lewis et al. ............ 530/406 |
| 5,168,057 | 12/1992 | Oh et al. ............ 435/174 |
| 5,196,351 | 3/1993 | Harris et al. ............ 436/501 |

FOREIGN PATENT DOCUMENTS

| | | |
|---|---|---|
| 0057731 | 8/1982 | European Pat. Off. . |
| 0310361 | 4/1989 | European Pat. Off. ... G01N 33/351 |
| 0315317 | 5/1989 | European Pat. Off. . |
| 8903042 | 4/1989 | WIPO ............ G01N 33/351 |

*Primary Examiner*—Kay K. A. Kim
*Attorney, Agent, or Firm*—William H. May; Arnold Grant; Stephen Donovan

[57] ABSTRACT

A method for making a valproic acid derivative comprising a functionalized spacer arm attached to a δ carbon atom of a valproic acid molecule is disclosed. The method proceeds by attaching a spacer arm joined to an inorganic moiety to a valproic acid precursor to make an alkylated compound, derivatizing the alkylated compound in a liquid medium to make the valproic acid derivative, and then separating the valproic acid derivative from the liquid medium. The valproic acid derivative can be used to make an immunoreactive valproic acid conjugate.

13 Claims, 2 Drawing Sheets

METHOD FOR MAKING VALPROIC ACID DERIVATIVES

BACKGROUND

We have invented a new method for making valproic acid derivatives. The valproic acid derivatives can be used to make immunoreactive valproic acid conjugates.

Valproic acid is a low molecular weight, saturated fatty acid with significant utility as an antiepileptic drug. Valproic acid is used to treat a variety of convulsant disorders, and is especially effective in the treatment of petit mal absence, generalized tonic-clonic seizures, and myoclonic disorders. Valproic acid administration has also resulted in substantial improvement of patients with Lennox syndrome, which is extremely resistant to almost all drug treatment. Significantly, unlike many other anticonvulsant drugs, a development of tolerance by a patient to the anticonvulsant effects of valproic acid does not typically occur. A lack of tolerance development means that drug efficacy can be maintained for a given level of administration. The optimal therapeutic range of valproic acid depends on a number of factors, including the method of administration, and the particular convulsant condition being treated, but generally lies between about 50 $\mu$g and about 100 $\mu$g per mL of serum.

The wide acceptance and medical use of valproic acid, combined with a low and narrow optimal therapeutic serum concentration, necessitates a fast and accurate procedure for monitoring the level of valproic acid in a patient's physiological fluids. Monitoring of a patient's serum valproic acid level can be critical to medical decision-making. Furthermore, a hospital or clinical environment can generate a substantial number of physiological fluid samples obtained from patients receiving valproic acid. Hence, a method to detect and quantify valproic acid levels in multiple test samples quickly and accurately is highly desirable.

Methods for detecting valproic acid in physiological fluids are limited in part because of the small size of the valproic acid molecule and because valproic acid shows essentially no absorption characteristics in the ultraviolet spectrum. Known methods for detecting valproic acid include gas-liquid chromatography, high pressure liquid chromatography and mass spectrometry. These methods require expensive instrumentation, extensive test sample preparation, and lengthly technician training. All these factors can impede and delay analysis of a test sample for valproic acid. Additionally, these methods are not suitable for the rapid and accurate analysis of the large number of patient test samples that can be generated by the valproic acid monitoring programs of many hospitals and convulsant treatment clinics. Hence, a simple, fast, and efficient method of detecting and quantifying valproic acid in multiple physiological fluids samples has been pursued.

Immunological assay methods have shown considerable utility for the detection and quantification of valproic acid in test samples. An immunoassay can be based upon the detection of an immunoprecipitation reaction. An immunoprecipitation reaction can occur when two reaction partners, each with a specific binding affinity for the other, are combined in a suitable liquid medium. The reaction partners can be an antigen and a specific binding partner for the antigen, such as an antibody. Once initiated in a liquid medium, the immunoprecipitation reaction results in the formation of immunoprecipitates, or antibody-antigen complexes in the liquid medium.

The presence of immunoprecipitates in the liquid medium can change optical properties, such as light scattering and light absorption properties of the liquid medium, due to attenuation of incident light energy by the immunoprecipitates. These changes can be detected by an appropriate photometer in a photometric immunoassay. Photometric immunoassay techniques include both nephelometric and turbidimetric techniques.

Various immunoassay methods to detect and quantify valproic acid in physiological fluid test samples are known to the art. An immunoassay of valproic acid or its metabolites, must overcome several problems. One of these problems arises because valproic acid is a hapten. Hence, valproic acid is not by itself capable of inducing an immune response upon administration to an animal body, including a human body. This occurs because valproic acid is too small to be recognized by the body's immune system. However, when coupled to a carrier, such as certain proteins, the valproic acid:carrier conjugate can act as an antigen which is large enough to induce valproic acid antibody production. These antibodies can then be used in an immunoassay for valproic acid.

The valproic acid molecule is typically not coupled directly to the carrier, because the larger carrier tends to prevent a valproic acid molecule that has been directly linked to the carrier from being recognized by an animal's immune system. Generally therefore, a valproic acid derivative is prepared for coupling to the carrier. The valproic acid derivative can be a valproic acid molecule attached to one end of a spacer arm or spacer chain of a sufficient length. The free end of the spacer arm, that is the end of the spacer arm that is not attached to the valproic acid molecule, usually bears a reactive functional group. The functional group is used to link the free end of the spacer arm to a carrier, such as bovine serum albumin, to make a valproic acid conjugate.

Interposed between the valproic acid molecule and the carrier, the spacer arm thereby acts to physically space or extend the valproic acid molecule away from the carrier. The valproic acid molecule can then be recognized by an animal's immune system as an immunogen. Hence, it is highly desirable to be able to prepare a valproic acid derivative which upon linkage to a carrier results in the making of an immunoreactive valproic acid conjugate.

Besides being useful to raise antibodies against valproic acid, an immunoreactive valproic acid conjugate can also be used as a developer antigen in a competitive inhibition immunoasay for valproic acid. A developer antigen is used because the small, monovalent valproic acid molecule is unable to form a large complex or aggregate with the valproic acid antibodies. Consequently, a valproic acid derivative, such as a biotinylated valproic acid derivative, can be conjugated to a carrier, such as avidin, to make a valproic acid developer antigen. The valproic acid developer antigen is another type of immunoreactive valproic acid conjugate. The valproic acid derivative is again typically made by attaching a spacer arm to a valproic acid molecule. The interposed spacer arm permits the antivalproic acid antibodies used in an immunoassay for valproic acid to recognise and adhere to the valproic acid component of the immunoreactive valproic acid conjugate. In this manner detectable immunoprecipitates can form.

Thus, formation of either the valproic acid immunogen, or the valproic acid developer antigen for use respectively, in raising valproic acid antibodies, or as the developer reagent in a competitive inhibition immunoassay for free valproic acid in a patient test sample, first requires that a suitable valproic acid derivative be prepared for conjugation to a carrier.

It would therefore be advantageous to have a method for easily preparing significant amounts of a valproic acid derivative suitable for conjugation to a carrier. The immunoreactive valproic acid conjugates can then be used to raise anti-valproic acid antibodies or as developer antigens in a valproic acid competitive inhibition immunoassay.

Existing methods for making a valproic acid derivative having a functionalized spacer arm have considerable deficiencies and drawbacks. Thus, it is known that a valproic acid derivative amenable to conjugation to a carrier, can be made by attaching a functionalized spacer arm to the $\alpha$ carbon atom of the valproic acid molecule. Unfortunately, an $\alpha$ position derivatized valproic acid molecule cannot be reliably used to make immunoreactive valproic acid conjugate for raising antivalproic acid antibodies. Additionally, a valproic acid conjugate made from an $\alpha$ position derivatized valproic acid molecule tends to have highly variable immunoreactivity from one batch of such a conjugate to another.

It is also known to make a valproic acid derivative by attaching a spacer arm to a $\delta$ carbon atom position of a valproic acid molecule. Such $\delta$ position derivatized valproic acid molecules have been used to make suitable immunoreactive valproic acid conjugates. Unfortunately, significant problems exist with known methods for attaching a functionalized spacer arm to a $\delta$ carbon atom of the valproic acid molecule. These problems include extreme difficulty to remove the alkylating reagent once it has attached the spacer arm to a precursor valproic acid molecule. Thus, when particular aromatic reagents, such as an alkylating phthalimide is used to attach a spacer arm, the aromatic molecule can be almost intractable to removal. Removal can require high temperature and dangerous closed system conditions.

Additionally, separation of the valproic acid derivative from the reaction medium and other reaction products, and unreacted reagents, can usually be carried out only by difficult and time consuming extraction procedures.

Furthermore, existing methods for making valproic acid derivatives suitable for formation into immunoreactive valproic acid conjugates, do not use the same valproic acid precursor starting material, to make more than one type of valproic acid derivative. Different valproic acid derivatives can have different spacer arms and/or spacer arm functional groups. The ability to make a variety of valproic acid derivatives from the same valproic acid precursor starting material is highly desirable for a number of reasons. For example, different spacer arms can allow precise control of steric factors, which in turn affect binding/unbinding characteristics of the valproic acid molecule of a valproic acid conjugate with different substrates and binding partners. Additionally, the ability to vary the spacer arm functional groups can permit the valproic acid derivative to be linked to different carriers.

What is needed therefore is a method for making a valproic acid derivative that allows: (1) the alkylating reagent to be removed under mild conditions subsequent to attachment of the spacer arm; (2) easy separation of the prepared valproic acid derivative from other reactants, and by-products; (3) a plurality of valproic acid derivatives to be made from the same valproic acid precursor starting material, and; (4) preparation of valproic acid derivatives that can be used to make immunoreactive conjugates.

SUMMARY

A method according to the present invention meets these needs. The disclosed method allows for removal of the alkylating reagent under mild conditions subsequent to attachment of the spacer arm, easy separation of the prepared valproic acid derivative from other reactants, and by products, and permits a plurality of valproic acid derivatives to be made from the same valproic acid precursor starting material. The prepared valproic acid derivatives made can be used to make immunoreactive valproic acid conjugates.

Definitions

The following definitions are provided to facilitate an understanding of the present invention. To the extent that these definitions may vary from meanings within the art, our definitions are to control.

"Aliphatic reagent" means a nonaromatic compound capable of alkylating a valproic acid precursor, and which comprises a spacer arm joined to an inorganic moiety.

"Alkylated compound" means a compound that results from reacting a valproic acid precursor with the aliphatic reagent. The alkylated compound comprises a spacer arm and an inorganic moiety bound to the spacer arm.

"Bidentate" or "bidentate conjugate" means a heterobifunctional conjugate with two chemical moieties, or bidentate members, attached by a spacer moiety, with each member being capable of specifically binding to a different macromolecule. Further definition and details regarding bidentate conjugates can be found in the copending U.S. Pat. No. 5,196,351 entitled "Novel Bidentate Conjugate and Method of Use Thereof", issued Mar. 23, 1993.

"Conjugate" means a compound formed by joining a valproic acid derivative to a carrier, thereby permitting the conjugate to be used as an immunogen or as a developer antigen. The carrier can comprise a smaller ligand molecule and a larger binding partner for the ligand.

"Derivatizing" an alkylated compound means carrying out the reaction or reactions to transform the alkylated compound into a valproic acid derivative.

"Ligand" means a molecule that can bind to the functionalized spacer arm of the valproic acid derivative to make a valproic acid preconjugate.

"Inorganic moiety" means a substance attached to a spacer arm, which substance is comprised at least in part of an inorganic atom or atoms.

"Spacer arm" means an saturated, aliphatic compound capable of being attached to a valproic acid precursor. "Functionalized spacer arm" means a spacer arm having a reactive group that can be used to link the spacer arm to a ligand.

"Valproic acid derivative" means a valproic acid molecule with a functionalized spacer arm attached to a $\delta$ carbon atom of the valproic acid molecule.

"Valproic acid preconjugate" means a valproic acid derivative bound to a ligand molecule.

"Valproic acid precursor" means a compound that can be used as a starting material to make a plurality of valproic acid derivatives.

A method according to the present invention for making a valproic acid derivative comprising a functionalized spacer arm attached to a δ carbon atom of a valproic acid molecule has two steps. The two steps are attaching a spacer arm joined to an inorganic moiety to a valproic acid precursor in an attaching reaction to make an alkylated compound, and transforming the alkylated compound into the valproic acid derivative by derivatizing the alkylated compound in a liquid medium. The valproic acid derivative made can then be separated from the liquid medium. The attaching reaction is carried out by reacting the valproic acid precursor with an aliphatic reagent.

A method according to the present invention for making a valproic acid derivative comprising a carboxylated spacer arm attached to a δ carbon atom of a valproic acid molecule preferably has the following steps. Firstly, reacting a valproic acid precursor with an aliphatic compound in an attaching reaction to make the alkylated compound. The aliphatic compound can include a haloester spacer arm. The attaching reaction being carried out for between about 2 hours to about 4 hours at a temperature between about 15° to about 25° C., followed by continuing the attaching reaction for between about 14 hours and about 18 hours at a temperature between about 50° and about 70° C. Secondly, hydrolysing the alkylated compound in a basic medium to obtain a carboxylated substance comprising a plurality of carboxyl groups. Thirdly, decarboxylating the carboxylated substance in an acidic medium to remove one of the carboxyl groups from the carboxylated substance to thereby make the valproic acid derivative comprising the carboxylated spacer arm attached to a δ carbon atom of the valproic acid molecule. The decarboxylating reaction is preferably carried out for between about 5 hours and about 15 hours. The final step is to separate the valproic acid derivative made from the acidic medium.

A method according to the present invention for making a valproic acid derivative comprising an aminated spacer arm attached to a δ carbon atom of a valproic acid molecule preferably has the following steps. Firstly, reacting the valproic acid precursor with the aliphatic compound in the attaching reaction to make the alkylated compound. The aliphatic compound can include a halocyanide spacer arm. The attaching reaction can be carried out for between about 2 hours to about 4 hours at a temperature between about 15° to about 25° C., followed by continuing the attaching reaction for between about 14 hours and about 18 hours at a temperature between about 50° and about 70° C. Secondly, hydrogenating the alkylated compound to obtain a hydrogenated alkylated compound, the hydrogenating step being carried out for between about 10 hours and about 14 hours at a pressure between about 30 PSI and about 60 PSI. Thirdly, hydrolysing the hydrogenated alkylated compound in an acidic medium to make the valproic acid derivative comprising the aminated spacer arm attached to a δ carbon atom of the valproic acid molecule. And fourthly, separating the valproic acid derivative made from the acidic medium.

An alternate preferred method for making a valproic acid derivative according to the present invention can have the steps of: selecting a valproic acid precursor comprising a tertiary substituted carbon atom; selecting a spacer arm comprising a first functional moiety and a second functional moiety; reacting the tertiary carbon with the spacer arm, thereby displacing the first functional moiety and attaching the spacer arm to the tertiary carbon, resulting in a valproic acid intermediate comprising a quaternary carbon atom bearing the spacer arm with the second functional moiety; derivatizing the valproic acid derivative to return the quaternary carbon to its former tertiary state, and transforming the second moiety into a reactive group, thereby making a valproic acid derivative comprising the spacer arm with the reactive group.

Also within the scope of the present invention is a method for making an immunoreactive valproic acid conjugate. A preferred method begins by preparing a valproic acid derivative as set forth above, followed by: joining the spacer arm of the valproic acid derivative to a ligand, to make a valproic acid preconjugate, and then combining the valproic acid preconjugate with a specific binding partner for the ligand, to make an immunoreactive valproic acid conjugate.

DRAWINGS

These and other features, aspects, and advantages of the present invention can become better understood from the following description, claims and the accompanying drawings where:

DESCRIPTION

Figure 1:
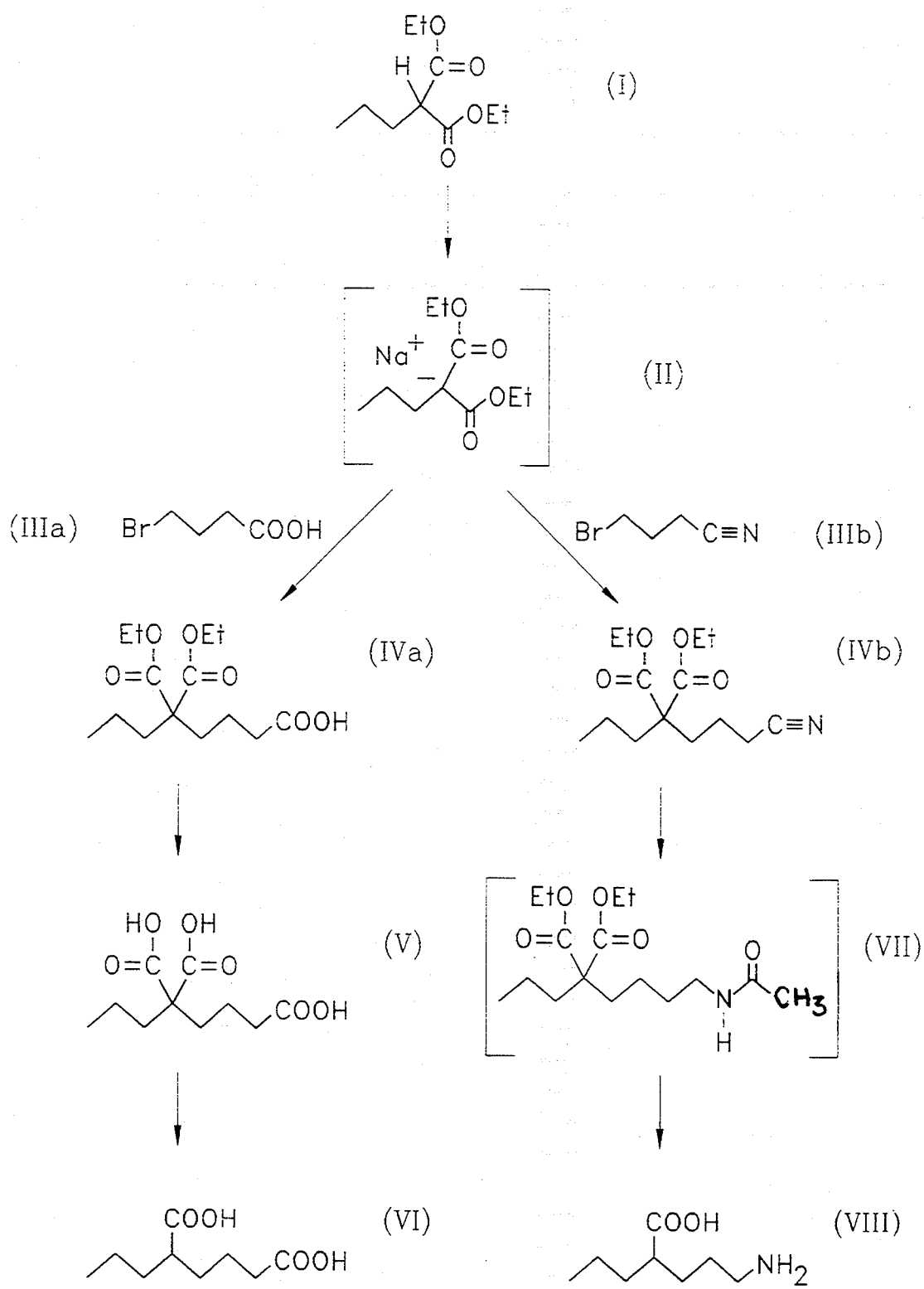
FIG. 1 illustrates a method according to the present invention for making carboxylated and aminated valproic acid derivatives.

We have discovered a simple two step method for making a variety of valproic acid derivatives. A method according to our invention uses the same valproic acid precursor starting material to make different valproic acid derivatives. The valproic acid molecule has the structure shown below:

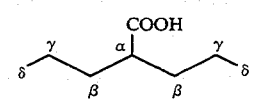

All the valproic acid derivatives made by our method have a functionalized spacer arm attached to a δ carbon atom of a valproic acid molecule. The valproic acid derivatives can be used to make immunoreactive valproic acid conjugates.

The method is characterized by attaching a spacer arm bearing an inorganic moiety to a valproic acid precursor in an attaching reaction to make an alkylated compound. The alkylated compound is then transformed into the desired valproic acid derivative.

The attaching reaction is carried out by reacting the valproic acid precursor with an aliphatic reagent. The aliphatic reagent comprises a spacer arm joined to an inorganic moiety. The transformation step is carried out by derivatizing the alkylated compound in a liquid medium. The term derivatizing is used to indicate the reaction or reactions that are required to transform the alkylated compound into the valproic acid derivative. The derivatization process, as set forth below, includes different reactions steps or sequences when different valproic acid derivatives are desired. Subsequent to the transformation step, the valproic acid derivative is separated from the liquid medium.

The Attaching Reaction

The attaching reaction results in the alkylated compound. The attaching reaction proceeds by reacting the valproic acid precursor starting material with the aliphatic reagent. The same valproic acid precursor is used to make a variety of different valproic acid derivatives. The valproic acid precursor can be any compound that has an n-propyl chain, or a moiety that can be easily made into an n-propyl chain, joined to a tertiary substituted carbon atom. Additionally, one of the substituents of the tertiary carbon atom must be capable of transformation into a carboxyl group, to provide the carboxyl group of the valproic acid molecule in the final valproic acid derivative.

The n-propyl chain of the valproic acid precursor is required to provide the n-propyl component of the valproic acid derivative. The tertiary substituted carbon atom provides an easily removable hydrogen, for carbanion formation during the attaching reaction. Carbanion formation during the attaching reaction, facilitates alkylation of the valproic acid precursor by the spacer arm of the aliphatic reagent.

Preferably, the valproic acid precursor is an $\alpha$-n-propyl, $\alpha$-$R_1$, $\alpha$-$R_2$-(CH) compound, where $R_1$ and $R_2$ are electron withdrawing groups, such as ester groups. Electron withdrawal facilitates removal of the tertiary carbon atom's hydrogen, thereby allowing carbanion formation during the attaching reaction. More preferably, the valproic acid precursor is a propylmalonate. Most preferably, the valproic acid precursor is a diester propylmalonate, such as diethylpropylmalonate (I), because such compounds are readily available and are suitable for making the desired valproic acid derivatives.

The aliphatic reagent provides the spacer arm for attachment to the tertiary carbon atom of the valproic acid precursor. The aliphatic reagent comprises the spacer arm and two inorganic moieties, a displaceable moiety and a functionalizable moiety. Preferably, the inorganic moieties are disposed one at each end of the aliphatic spacer arm. The displacable moiety is displaced during the attaching reaction when a carbanion valproic acid precursor is formed, permitting that end of the spacer arm, from which the inorganic moiety is displaced, to become attached to the tertiary carbon atom of the valproic acid precursor. The tertiary carbon atom thereby becomes a quaternary carbon atom, with four substituent groups. The functionalizable inorganic moiety remains joined to the spacer arm subsequent to the attaching reaction. The functionalizable moiety can be derivatized into a suitable functionality, such as a carboxyl group or an amino group, thereby providing the functional group of the functionalized spacer arm of the valproic acid derivative.

Preferably, the spacer arm is a saturated, aliphatic chain at least four carbon atoms in length in order to provide the second n-propyl chain of the valproic acid molecule of the valproic acid derivative, and at least a one carbon atom extension of a carbon $\delta$ atom of the valproic acid molecule. More preferably, the spacer arm is a saturated aliphatic carbon chain of from 4 to about 20 carbon atoms in length. Fewer than 4 carbon atoms in the spacer arm provides a spacer arm with an insufficient steric effect. A spacer arm with more than about 20 carbon atoms tends to lose the benefit of association with a carrier. Most preferably, the spacer chain is from about 4 to about 8 carbon atoms in length. Spacer arms of such length are preferred because the functionalized group which is preferably at the end of an extended chain of the $\delta$ carbon atom, is used to attach the valproic acid derivative to a carrier molecule or ligand such as biotin. The spacer arm therefore acts to provide at least part of a steric distancing between the carrier molecule and the valproic acid molecule in a valproic acid conjugate. In this manner the valproic acid conjugate can be immunoreactive because the spacer arm allows the valproic acid molecule to extend away from the carrier molecule. Thus, the immunoreactive valproic acid conjugate prepared can be used as an immunogen to raise anti-valproic acid antibodies, or as a developer antigen in a competition inhibition immunoassay.

Particular spacer arm compositions, length, and constructions in conjunction with particular carrier molecules used for conjugate formation, are set forth in the copending U.S. Pat. No. 5,196,351 entitled "Novel Bidentate Conjugate and Method of Use Thereof" issued Mar. 23, 1993, which is incorporated herein in its entirety.

The displaceable inorganic moiety of the aliphatic reagent preferably comprises a halogen, because halogens are easily displacable and can be used to make effective alkylating reagents. More preferably, the displaceable inorganic moiety is a single halogen atom such as a bromine atom, because single halogen atom displaceable moieties permit construction of highly effective alkylating reagents.

The functionalizable inorganic moiety of the aliphatic reagent remains attached to the spacer arm after the spacer arm has become attached to the valproic acid precursor. Thus, the functionalizable inorganic moiety is the precursor of the final functional group on the $\delta$ carbon atom chain attached to the valproic acid molecule of the valproic acid derivative. As such the functionalizable moiety is chosen so as to be transformable into the desired final spacer arm functional group. Thus, as ester can be used as the functionalizable inorganic moiety when the final desired functional group, of the spacer arm attached to the $\delta$ carbon atom of the valproic acid derivative, is a carboxyl group. Similarity, the functionalizable inorganic moiety can be a cyano group where the final desired functional group, of the spacer arm attached to the $\delta$ carbon atom of the valproic acid derivative, is an amino group.

The functionalizable inorganic moiety is preferably not an aromatic group such as a phthalimide group, because aromatic groups in general and phthalimide groups in particular can be extremely difficult to functionalize and to remove from the valproic acid precursor during the transformation step.

Most preferably, the aliphatic reagent is a haloester or a halocyanide to combine the above-indicated advantages of a halogen as the displaceable moiety with a suitable functionalizable inorganic moiety.

The first step of the attaching reaction is to abstract the hydrogen atom from the tertiary substituted carbon atom of the valproic acid precursor. Hydrogen atom abstraction results in activation of the valproic acid precursor and formation of a carbanion. A suitable activation solution solubilizes the aliphatic compound, and the valproic acid precursor in a liquid medium, and provides an activation reagent. The activation reagent can disassociate into an anion that facilitates abstraction of the tertiary carbon atom hydrogen atom. A suitable activation solution is dimethylformamide (DMF). Preferably, the activation reagent comprises a metal hydride, such as a sodium hydride. A more preferred activation reagent is sodium hydride because of its commercial availability and ability to easily dissociate into a hydride anion. Subsequent to activation, the aliphatic compound is reacted with the activated valproic acid precursor.

After addition of the aliphatic reagent, the attaching reaction is preferably carried out for a first period of time at a first temperature, followed by continuing the attaching reaction for a second longer period of time at a second higher temperature. The purpose of this two step alkylation procedure is to allow the reagents to mix and the exothermic activation process to take place in the first step, followed by the second step during which the reaction is allowed to proceed to or essentially to completion. More preferably, the attaching reaction is carried out for between about 2 hours and about 4 hours at a temperature between about 15° and about 25° C., followed by continuing the attaching reaction for between about 14 hours and about 18 hours at a temperature between about 50° and about 70° C. These temperature and time periods can be used because they have been found to facilitate both the first step reagent mixing and activation process, and completion of the reaction in the second step of the alkylation procedure.

Transformation

The alkylated compound resulting from completion of the attaching reaction is transformed into the valproic acid derivative by a derivatization process. Derivitization can include a step of hydrolysing the alkylated compound to obtain a carboxylated substance. The hydrolysing step can be carried out in a basic medium or in an acidic medium. The carboxylated substance made by the hydrolysing reaction can be a valproic acid derivative with an aminated spacer arm or the carboxylated substance can be an alkylated compound with a plurality of carboxyl groups. When the latter compound is obtained, the transformation step includes the step of decarboxylating the carboxylated substance to obtain a valproic acid derivative with a carboxylated spacer arm. The decarboxylating step is preferably carried out in an acidic medium.

The transformation step can also include the step of hydrogenating the alkylated compound. Hydrogenation of the alkylated compound can be carried out for between about 10 hours and about 14 hours, and at a pressure between about 30 PSI and about 60 PSI.

The transformation step can proceed by, for example: (1) hydrolysis followed by decarboxylation (Transformation I), or; (2) hydrogenation followed by hydrolysis (Transformation II). Both Transformations I and II result in the bonding of a plurality of hydrogen atoms to the alkylated compound.

Transformation I proceeds by hydrolysing the alkylating compound to obtain a carboxylated substance, and by then functionalizing the functionalizable inorganic moiety. Hydrolysis is preferably carried out in a basic medium to facilitate transformation of the inorganic moiety. Subsequent to hydrolysis, the carboxylated substance is decarboxylated to obtain the valproic acid derivative. Decarboxylation is preferably carried out in an acidic medium to favor the decarboxylation reaction.

Transformation II proceeds by hydrogenation of the alkylated compound. Hydrogenation is preferably carried out at an elevated atmospheric pressure to accelerate the hydrogenation reaction. More preferably, the hydrogenation is carried out for a time period of between about 10 hours and about 14 hours at an atmospheric pressure of between about 30 PSI and about 60 PSI. Subsequent to hydrogenation, the hydrogenated compound is hydrolysed to obtain the valproic acid derivative. Preferably, hydrolysis is conducted in an acidic medium to facilitate functionalization of the inorganic moiety. Separation of the valproic acid derivative resulting from the transformation step is easily accomplished by removing the solvent for the transformation step. This can be carried out by evaporating the solvent.

FIG. 1 illustrates the attaching and transformation steps of our method with particular starting materials. Diethylpropylmalonate (I) can be used as the valproic acid precursor. Mixing the diethylpropylmalonate (I) with a suitable activation solution results in formation of the carbanion (II). A brominated aliphatic reagent (IIIa or IIIb) can then be added to the carbanion (II), to make the alkylated compound (IVa or IVb), thereby completing the attaching reaction. Transformation I then proceeds by base hydrolysis of IVa to obtain a carboxylated substance (V). The carboxylated substance (V) can then be decarboxylated in an acidic medium to obtain a valproic acid derivative with a carboxylated spacer arm (VI). The spacer arm of the aliphatic reagent, and as attached to the valproic acid derivative is shown by in FIG. 1, indicating that the spacer arm can be from about 4 to about 20 carbon atoms in length.

Transformation II is also illustrated by FIG. 1. After the attaching reaction, the alkylated compound (IVb) is transformed by reductive hydrogenation into an intermediate (VII). The intermediate VII can then by subjected to acid hydrolysis to obtain a valproic acid derivative with an aminated spacer arm (VIII). Product VIII can also be referred to as a carboxylated substance.

Figure 2:
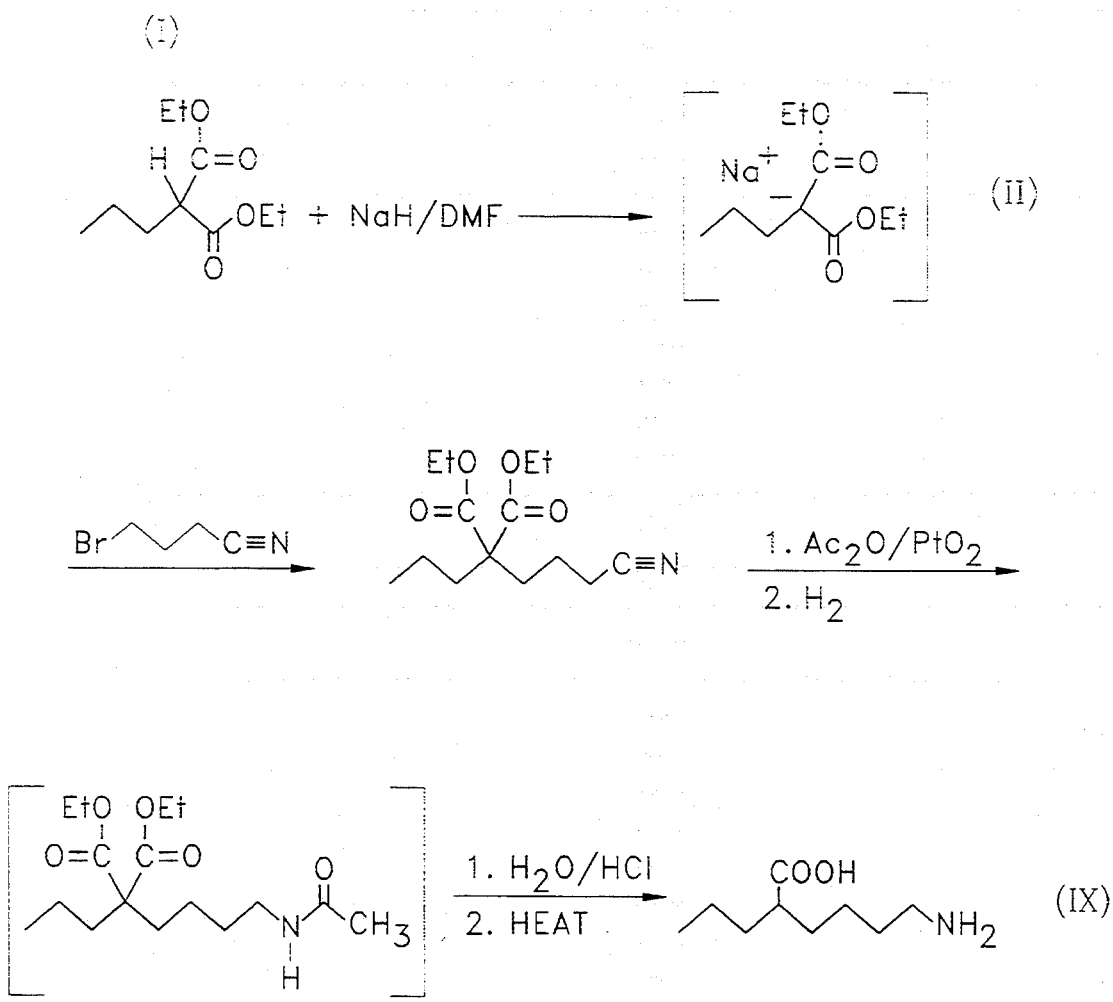
FIG. 2 illustrates a method according to the present invention for making the aminated valproic acid derivative, 6-amino-2-n-propyl hexanoic acid.

FIG. 2 illustrates the synthetic route according to the present method for obtaining a particular aminated valproic acid derivative (VIII), 6-amino-2-n-propylhexanoic acid (IX). As shown by FIG. 2, diethylpropylmalonate (I) can be activated by sodium hydride in dimethyformamide (NaH/DMF), followed by alkylation by with bromobutyronitrile (a IIIb type aliphatic reagent). The alkylated compound obtained, ethyl-2-carbethoxy-2-propyl-5-cyanopentanoate (a species of IVb), can then be transformed into the valproic acid derivative, 6-amino-2-n-propylhexanoic acid (IX) by a derivatization process that includes firstly reductive hydrogenation of the ethyl-2-carbethoxy-2-propyl-5-cyanopentanoate in acetic anhydride with platinum oxide as catalyst, followed by hydrogenation at an elevated pressure (Ac$_2$O/PtO$_2$, H$_2$). The next step in the derivatization process shown in FIG. 2 is acid hydrolysis (H$_2$O/HCL, heat) to obtain the aminated valproic acid derivative indicated.

The valproic acid derivative, 6-amino-2-n-propylhexanoic acid (IX) was conjugated to apoferritin and used as a developer antigen in a nephelometric immunoassay of multiple patient serum test samples for valproic acid.

A number of valproic acid derivatives were made by the present method, including: 6-amino-2-n-propylhexanoic acid (6-amino-2-n-propylcaproic acid) (IX); 2-n-propyl-1,7-heptanediioc acid, and; 2-n-propyl-1,9-nonanediioc acid, which was conjugated to bovine serum albumin and used to successfully raise anti-valproic acid antibodies.

Immunoreactive Conjugates

The prepared valproic acid derivative can be conjugated to a carrier or ligand to form a valproic acid preconjugate. The valproic acid preconjugate can then be attached to a specific binding partner for the ligand to form the immunoreactive valproic acid conjugate. The specific binding partner can be a protein. The conjugate can be used to raise antibodies against valproic acid by injecting the conjugate, as an antigen, into an animal body and then harvesting the valproic acid antibodies made by the animal. In this manner, goat anti-valproic acid sera were produced by administrating goats with various valproic acid derivatives prepared by the disclosed method, including 2-n-propyl-1,9-nonanedioic acid conjugated to bovine serum albumin (BSA).

A valproic acid derivative made according to the present invention can also be used to make an immunoreactive valproic acid conjugate that can be used as a developer antigen in a competitive inhibition immunoassay for free valproic acid in a test sample. A biotin-valproic acid bidentate can be prepared by coupling biotin to an amino derivative of valproic acid, 6-amino-2-n-propylhexanoic acid, via two aminocaproic acid linkages. Further details of bidentate conjugate formation can be found in copending U.S. Pat. No. 5,196,351 issued Mar. 23, 1993. For example, a particular valproic acid bidentate, N-[N'-(N''-biotinoyl-6-aminocaproyl)-6-aminocaproyl]-2-n-propyl -6-aminocaproic acid, consisting of a biotin group and a 2-n-propyl-6-aminocaproic acid group separated by two 6-aminocaproic acid spacers was made by biotinylating a valproic acid derivative made by the present method, 6-amino-2-n-propyl hexanoic acid. The was accomplished by first activating N-(N'-biotinoyl-6-aminocaproyl)-6-aminocaproic acid with carbonyldiimidazole (CDI) in N-hydroxysuccinimide (NHS), followed by coupling to the 6-amino-2-n-propylcaproic acid (also called 6-amino-2-n-propylhexanoic acid).

EXAMPLES

The following examples are set forth as illustrations of various features and embodiments of the invention and are not intended to limit the scope of the claimed invention.

Example 1

(Synthesis of ethyl-2-carbethoxy-2-propyl-5-cyano pentanoate)

Ethyl-2-carbethoxy-2-propyl-5-cyano pentanoate was made as follows. Into a dry 250 mL, 3-neck flask equipped with a stir bar, condenser, nitrogen inlet, and an additional funnel, there was placed 3.12 g (0.078M) of sodium hydride (NaH) (formula weight (FW 24) as a 60% dispersion in mineral oil (obtained from Aldrich chemical company).

Next, 50 mL of dry DMF (anhydrous 99+%; F.W.; 73.10; B.P.; 153° C.; d 0.945) (Aldrich) was introduced under nitrogen. To the stirred solution 12.15 g (0.06M; d 0.987; FW 202.25; 12.3 mL) of diethylpropylmalonate (99%, FW 202.25; BP 221°-222° C., d 0.987; n 1.4185) (Aldrich) was slowly added to the flask through the addition funnel. Stirring was continued for 1 hour, until hydrogen stopped being evolved and no solid NaH remained. This was followed by slowly adding through the addition funnel to the stirred solution, 6.075 mL (0.0625M; 9.25 g) of bromobutyronitrile (97%; FW 148.01; BP 205° C., d 1.4780, n 1.4780) (Aldrich) in 13 mL of DMF.

Stirring was continued for 3 hours at room temperature, and then for 16 hours at 60° C. The solvent was then removed by rotary evaporation. Chloroform (100 mL) was then added, followed by extraction with two 50 mL portions of water. The aqueous layer was then extracted with 50 mL of chloroform and was combined with the previous chloroform extract. The chloroform solution was dried over anhydrous magnesium sulfate, filtered and concentrated to obtain 17.4 g of a light yellow oil. The oil was distilled under vacuum to obtain the desired reaction product ethyl-2-carbethoxy-2-propyl-5-cyano pentanoate (FW 269.35).

Example 2

(Synthesis of 6-amino-2-n-propyl hexanoic acid)

6-amino-2-n-propyl hexanoic acid was made as follows. Into a dry 500 mL hydrogenation bottle there was placed 140 mL of acetic anhydride (Aldrich) (99+%; FW 102.09; BP 138°-140° C.; d 1.082) (distilled from anhydrous sodium acetate, FW 82.03 (Mallinckrodt)) and 25.3 g (93.9 mM) of the ethyl-2-carbethoxy-2-propyl-5-cyano pentanoate obtained by following the procedure of Example 1. Platinum (IV) oxide catalyst (842 mg; amorphous; FW 227.09) (Aldrich) was then introduced under nitrogen. The reaction mixture was placed on the Parr hydrogenator and the vessel flushed 3 times with hydrogen. The vessel was then filled to 45 PSI and shaking was started. Hydrogenation was continued overnight with shaking at room temperature. The catalyst was removed by filtering through celite.

The filtrate obtained was slowly added through an adition funnel to a solution of 170 mL concentrated HCL and 42 mL of water contained in an ice bath. This reaction solution was then brought to room temperature and refluxed under nitrogen. The solvent was removed and 100 mL of water was added. The pH was then adjusted to 1 with concentrated HCL and the aqueous layer was extracted with 4×150 mL chloroform. The pH was then adjusted to 13 with 6M NaOH and the aqueous layer was extracted with 4×150 mL chloroform. The pH was then adjusted to 6 with concentrated HCL and the aqueous layer was extracted with 4×150 mL chloroform. The solvent of the final aqueous layer was removed leaving a white solid. This white solid was triturated, heated and filtered using methanol. This solution was dried onto 10 g silica gel and placed on a column chromatography 2.5×60 cm column packed with silica gel (prepared as a 1/1 methanol/chloroform slurry), eluted with methanol/chloroform 7/3 to 8/2, and appropriate fractions, as determined by TLC, pooled to obtain the desired reaction product 6-amino-2-n-propyl hexanoic acid (FW 172.23).

Example 3

(Preparation of N-(N'-Biotinoyl-6-aminocaproyl)-6-aminocaproic acid)

N-(N'-Biotinoyl-6-aminocaproyl)-6-aminocaproic acid) was made by a four step process as follows.

A. The first step was to protect 6-aminocaproic acid using benzyl chloroformate to give N-benzyloxycarbonyl-6-aminocaproic acid. This first step was carried out as follows. A solution of 6-aminocaproic acid (32.8 g, 0.25M) in 75 mL of H₂O and 42 mL of 6N NaOH was cooled in a salt-ice bath to below 10° C. With stirring, benzyl chloroformate, 46.9 g, 0.275M) and 2N NaOH (138 mL) were alternatively added in small portions over 90 min. After the addition was complete, the solution was brought to room temperature, and stirring was continued for an additional 1 hr. The product was precipitated by lowering the pH to 2 with concentrated HCL, and H₂O was added as required to keep the suspension stirring. The white precipitate was filtered, then resuspended and triturated with 1 liter of water. The solid was filtered, washed with water, compressed and then washed with hexane. The solid was then thoroughly dried in a vacuum desiccator to yield 55 grams (83% yield) of N-benzyloxycarbonyl-6-aminocaproic acid.

B. The second step was to activate the N-benzyloxycarbonyl-6-aminocaproic acid obtained by following the procedure of Example 3 A. above, with ethyl chloroformate followed by reaction with a second 6-aminocaproic acid linker to yield N-(N'-benzyloxycarbonyl-6-aminocaproyl)-6-aminocaproic acid. This second step was carried out as follows. A solution of 52.1 g (0.19M) of N-benzyloxycarbonyl-6-aminocaproic acid (thoroughly dried) dissolved in 640 mL of toluene and 20 mL of triethylamine, was cooled to between −5° to −10° C. in an isopropanol/dry ice bath before ethyl chloroformate (19.1 mL, 0.199M) was slowly added to give a white precipitate. The precipitate was removed by filtration and discarded. To the filtrate cooled in an ice-water bath there was added over 45 minutes a solution of 25.7 g (0.19M) of 6-aminocaproic acid in 100 mL of cold 2N NaOH. After stirring for 1 hr at 0° C. and then overnight at room temperature, the pH was adjusted to 8 with 6N NaOH and 1.2 L of H₂O was added. The 1.3 L aqueous phase was washed with ethyl ether (3×200 mL), cooled in an ice bath, and acidified with concentrated HCL to give a white solid. The solid was filtered, thoroughly washed with water and stored in a desiccator. The partially dried solid was treated with 350 mL of hot ethyl acetate to give two layers. The ethyl acetate layer was dried (Na₂SO₄), filtered, concentrated to about 250 mL, and cooled to 4° C. to yield 19 g (27% yield) of N-(N'-benzyloxycarbonyl-6-aminocaproyl)-6-aminocaproic acid.

C. The third step was to carry out a reductive cleavage of the N-(N'-benzyloxycarbonyl-6-aminocaproyl)-6-aminocaproic acid obtained by following the procedure of Example 3 B. above, by hydrogenation to obtain a bis-aminocaproic acid, N-(6-aminocaproyl)-6-aminohexanoic acid. This third step was carried out as follows. To a solution of 8 g (21.14 mM) of N-(N'-benzyloxycarbonyl-6-aminocaproyl)-6-aminocaproic acid in 200 mL of methanol there was added a catalytic amount (two spatulas) of 5% palladium on activated charcoal under a nitrogen blanket. After 90 minutes at ambient temperature and pressure, hydrogenation was complete as monitored by TLC (90% CHCl₃/MeOH), which indicated the disappearance of N-(N'-benzyloxycarbonyl-6-aminocaproyl)-6-aminocaproic acid under UV, and the presence of an amine product with ninhydrin spray. The catalyst was removed by filtration, and the resulting solution was evaporated in vacuo to give 4 g of a bis-aminocaproic acid; N-(6-aminocaproyl)-6-aminohexanoic acid as a white solid: mp 188°–192° C. Evaporation of the filtrate and recrystalization yielded a second crop of the product, 0.54 g. Total yield, 88%.

D. The fourth step was to react the bis-aminocaproic acid obtained from Example 3C. above with the with an activated biotin-N-hydroxysuccinimide ester to obtain the desired product N-(N'-biotinoyl-6-aminocaproyl)-6-aminocaproic acid). This fourth step was carried out as follows.

Biotin (1.3 g, 5.33 mM) was dissolved at 70°–75° C. in 40 mL of DMF, and 1,1'-carbonyldiimidazole (993 mg. 6.127 mM) was added. After 30 min, the solution was brought to room temperature before N-hydroxysuccinimide (705 mg, 6.127 mM) and DMF (2,mL) were introduced. To the activated biotin formed after 15 hr was then added a solution of 1.3 g (5.33 mM) of the bis-aminocaproic acid; N-(6-aminocaproyl)-6-aminohexanoic acid, obtained from step C. above, in 0.2M NaHCO₃ (33 mL). The resulting reaction mixture, which became cloudy after 3 hr, was stirred overnight and let stand over the weekend at room temperature. The white solid formed was filtered, triturated with acidic H₂O, refiltered, washed with H₂O, and dried to give 1.354 g of N-(N'-Biotinoyl-6-aminocaproyl)-6-aminocaproic acid. The filtrate was stripped to dryness, dissolved in 8 mL of H₂O, lowered to pH 2 with 1N HCl, and collected by filtration to give a second crop (0.764 g) of the desired reaction product N-(N'-Biotinoyl-6-aminocaproyl)-6-aminocaproic acid. The product was checked for purity by TLC (90% CHCl₃/MeOH), and positive to both ninhydrin and cinnamaldehyde sprays. Total yield: 84%.

Example 4

(Preparation of N-(N'-N''-biotinoyl-6-aminocaproyl)-6-aminocaproyl)-2-n-propyl-6-aminocaproic acid)

N-(N'-N''-biotinoyl-6-aminocaproyl)-6-aminocaproyl)-2-n-propyl-6-aminocaproic acid, a biotinylated 6-amino-2-n-propyl hexanoic acid was made as follows. A solution of N-(N'-Biotinoyl-6-aminocaproyl)-6-aminocaproic acid (0.3 g, 0.638 mM) obtained by following the procedure of example 3 D. above, was dissolved in 25 ml of DMF was prepared by heating the mixture at 70° C. for 30 minutes, There was then added 135 mg (0.83 mM) of 1,1-carbonyldiimidazole. After a further 30 minutes, the solution was allowed to cool to room temperature, and N-hydroxysuccinimide (95 mg, 0.83 mM) and 2 mL of DMF were added. Stirring was continued for 15 hr at room temperature followed by the addition to the activated biotin solution of a solution of 170 mg (0.988 mM) of the 6-amino-2-n-propyl hexanoic acid, obtained by following the procedure of Example 2 above, in 1.7 mL of 0.5M sodium bicarbonate and stirred overnight at room temperature. The reaction solution was then concentrated to dryness, dissolved in methanol, and precipitated with ethyl acetate. The precipitate was filtered, and chromatographed on a silica gel column using 0–22.5% methanol/chloroform. Fractions were monitored by TLC (using 25% methanol in chloroform), and those fractions containing the product as judged by both its positive reaction to cinnamaldehyde spray and its lower Rf value (Rf=0.4–0.5) as compared to biotin's (Rf=0.6–0.7) were pooled. The pooled fraction was further purified by preparative TLC using 25% methanol in chloroform. Further purification by recrystalization from methanol/ethyl acetate yielded 120 mg of the valproic acid derivative bidentate; N-(N'-N''-biotinoyl-6-aminocaproyl)-6-aminocaproyl)-2-n-propyl-6-aminocaproic acid.

Example 5

(Preparation of avidin-biotin-6-amino-2-n-propyl hexanoic acid)

A number of avidin-biotin-6-amino-2-n-propyl hexanoic acid conjugates were prepared, including the conjugate made by the procedure set forth in this Example. Avidin (100 mg; 1.44 µM; 13.9 U/mg) (Boehringer Mannheim) was placed in a 20 mL vial and dissolved in 10 mL of 0.1M phosphate buffer pH 7.4. HABA (2-(4-hydroxyphenyl-azo)-benzoic acid) (50 µL; 10 mM) in phosphate buffer was then added to the avidin solution. HABA is used as a color end point indicator to monitor the amount of biotinylated valproic acid required to bind to the avidin. Biotinylated 6-amino-2-n-propyl hexanoic acid (MW 625; 0.905 mg) at 5 mg/mL in methanol was then added dropwise to the avidin-HABA solution, mixing between drops until the solution became light yellow, followed by adding a 10% excess. The mixture was then allowed to stand for 1 hour.

The conjugate concentrate was then dialyzed by being transferred to a 25 mm, 12–14,000 MW cutoff using 0.5 mL of citrate buffered saline (CBS) pH 6.0. Dialysis was carried out at 4°C. in the CBS, 70 X volume, with 6 changes in 3 days. The resulting avidin-biotin-6-amino-2-n-propyl hexanoic acid conjugate was diluted in the ICS ™ diluent and was then used in competitive inhibition immunoassays for valproic acid.

Example 6

(Immunoreactivity of the avidin-biotin-6-amino-2-n-propyl hexanoic acid conjugate)

The avidin-biotin-6-amino-2-n-propyl hexanoic acid conjugate prepared by following the procedure of Example 5 was titered with a valproic acid goat antibody using a Beckman ICS ® nephelometer and was found to be an immunoreactive conjugate.

Valproic acid standard curves (light absorption rate units vs. concentration of valproic acid, in µg/ml) were established. Appropriate calibrators were also prepared.

Additionally, cross-reactivity studies against numerous compounds showed that the prepared valproic acid conjugate retains immunogenic utility despite the presence of various cross reactants in the competitive inhibition immunoassay medium.

A rate nephelometric biotin-avidin immunoassay for the measurement of valproic acid in serum was carried out on a Beckman ARRAY ® 360 nephelometer. The assay featured a biotin labeled valproic acid conjugate, a goat anti-valproic acid serum, avidin, and human serum calibrators. The system measured the rate of nephelometric response or formation of light scattering due to antibody-conjugate-avidin complexing. Valproic acid, when present in the reaction medium, inhibits the complexation by competing with the conjugate for the antibody and results in reduction of signal response. Thus, the rate of nephelometric response is inversely proportional to the concentration of valproic acid in the specimen.

Reproducible results were obtained over the range of 10 to 150 µg/mL. Within-run coefficient of variation (CV) was less than 3% and between-run CV was less than 5% for samples containing valproic acid concentrations of 20 to 120 µg/mL. Correlation (N=78 samples) with a commercial fluorescence polarization kit gave the following regression equation: r=0.993, y=1.04+0.8. Interference studies indicated negligible effect at concentrations of up to 100 mg/dL hemoglobin, 14 mg/dL bilirubin, and 700 mg/dL triglycerides.

Example 7

(Synthesis of diethyl-2-propyl-2-carbethoxy-1,7-heptadioate)

Diethyl-2-propyl-2-carbethoxy-1,7-heptadioate was made as follows. Into a 250 mL 3 neck flask equipped with a 50 mL addition funnel, stirring bar, condenser, $N_2$ inlet tube and septum there was placed 6.25 g (0.156M) of NaH (60% in mineral oil). Next, 100 mL of dry DMF was introduced (distilled from CaH). To the stirred solution there was slowly introduced 25.3 g (0.125 Moles) of diethylpropylmalonate. Stirring was continued for 1 hour until $H_2$ was no longer evolved. To the stirred solution there was slowly introduced 26.16 g (0.125 Moles, 19.8 mL) of ethylbromovalerate in 25 mL of DMF. Stirring was continued for 3 hours at room temperature.

The solution was then stirred for 16 hours at 60° C. The solvent was then removed under vacuum. Chloroform (250 mL) was then added. The chloroform layer was then extracted with 200 mL, then with 100 mL of water. The aqueous layer was then extracted with 100 mL of chloroform, and this was combined with the previous chloroform extract, followed by being dried over magnesium sulfate to remove the solvent, leaving a dark oil. The oil was distilled under vacuum to obtain 32.2 g of the desired reaction product diethyl-2-propyl-2-carbethoxy-1,7-heptadioate.

Example 8

(Synthesis of 2-propyl-2-carboxy-1,7-heptadioic acid)

2-propyl-2-carboxy-1,7-heptadioic acid was made as follows. Into a 500 mL round bottom flask with a condenser there was placed 30 g of diethyl-2-propyl-2-carbethoxy-1,7-heptadioate obtained by following the procedure of Example 7, 150 mL of 6M sodium hydroxide, and 150 mL of methanol. The mixture was refluxed overnight to obtain a homogeneous solution. The methanol was then removed, and 100 mL of water was added. Extraction was then carried out with 2×200 mL of chloroform, and the extracts were discarded. The pH of the solution was then adjusted to 2 with 6M HCl and the solution was extracted with six 250 mL lots of ethyl acetate. The ethyl acetate extract was then dried over magnesium sulfate, and the solvent was removed leaving a colorless oil which solidified on standing. The desired reaction product, 2-propyl-2-carboxy-1,7-heptadioic acid (19.44 g, yield 87.5%) was thereby obtained.

Example 9

(Synthesis of 2-propyl-1,7-heptandioic acid)

2-propyl-1,7-heptandioic acid was made as follows. Into a 500 mL round bottom flask equipped with a condenser and drying tube, there was added 13.0 g of the 2-propyl-2-carboxy-1,7-heptadioic acid obtained by following the procedure of Example 8, 100 mL of dioxane and 100 mL of 6M HCl. The solution was refluxed overnight. The next day the dioxane was removed. The pH of the solution was then adjusted to 1.0 with 6M sodium hydroxide, and the water was removed.

The remaining residue was taken up with 300 mL of ethyl acetate, dried over magnesium sulfate and the solvent was then removed leaving a heavy yellow oil.

The oil was then distilled under vacuum to obtain 4.81 g (45.1% yield) of the desired reaction product, 2-propyl-1,7-heptandioic acid.

A method according to the present invention has many advantages, including the following:

1. The method requires only two steps to make a valproic acid derivative.
2. The method allows for easy functionalization of a spacer arm attached of a valproic acid derivative.
3. The same starting material, a valproic acid precursor, can be used to make a variety of different valproic acid derivatives.
4. The valproic acid derivatives made by the method can be used to prepare immunoreactive valproic acid conjugates.
5. The method makes use of commercially available and inexpensive starting materials and reagents.

Although the present invention has been described in considerable detail with regard to certain preferred embodiments thereof, other embodiments within the scope of the teachings of the present invention are possible. For example, the disclosed method can be used to prepare a wide diversity of valproic acid derivatives with different functionalized spacer arms extending a δ carbon atom of a valproic acid molecule.

Accordingly, the spirit and scope of the appended claims should not be limited to the descriptions of the preferred embodiments contained herein.

We claim:

1. A method for making a valproic acid derivative comprising the steps of:
   (a) reacting a valproic acid precursor with an aliphatic reagent to make an alkylated valproic acid precursor, wherein;
      (i) said valproic acid precursor consists essentially of a tertiary substituted carbon atom, the tertiary substitutions being n-propyl, $R^1$, and $R^2$, where $R^1$, and $R^2$ are ester groups, and;
      (ii) said aliphatic reagent consists essentially of an aliphatic chain between four carbons and twenty carbons in length, the aliphatic chain having an inorganic, displaceable and reactive moiety at one end of the aliphatic chain, the reactive moiety being displaced during reaction with the tertiary substituted carbon atom of the valproic acid precursor carbanion intermediate, and a moiety at the other end of the aliphatic chain selected from the group consisting of cyano functionalities capable of hydrolyzing to form an amino functionality and functionalities capable of hydrolyzing to form a carboxy functionality;
   (b) transforming the alkylated valproic acid precursor into a valproic acid derivative by hydrolyzing the alkylated valproic acid precursor in a liquid medium, and;
   (c) separating the valproic acid derivative from the liquid medium, the valproic acid derivative consisting essentially of a valproic acid molecule having,
      (i) an α-n-propyl group;
      (ii) a carboxylic acid group; and
      (iii) an α-saturated aliphatic chain of at least four carbons in length, wherein the free end of the saturated aliphatic chain is attached to the moiety hydrolyzed to form a functionality selected from the group consisting of an amino functionality and a carboxy functionality, the saturated aliphatic chain thereby providing at least a one carbon atom extension of a δ carbon atom of the valproic acid molecule.

2. The method of claim 1, wherein reacting a valproic acid precursor with an aliphatic reagent is carried out for a length of time of between about 2 hours to about 4 hours at a temperature of between about 15° C. to about 25° C., and for a length of time of between about 14 hours and about 18 hours at a temperature of between about 50° and about 70° C.

3. The method of claim 1, wherein the transforming step comprises the step of hydrolyzing the alkylated valproic acid precursor in a basic pH medium to obtain a carboxylated substance.

4. The method of claim 1, wherein the transforming step comprises the step of hydrolyzing the alkylated valproic acid precursor in an acidic pH medium to obtain a carboxylated substance.

5. The method of claim 1, wherein the transforming step comprises the step of hydrogenating the alkylated valproic acid precursor.

6. The method of claim 5 wherein the hydrogenating step is carried out for a length of time of between about 10 hours and about 14 hours at a pressure of between about 30 PSI and about 60 PSI.

7. The method of claim 1, wherein the aliphatic reagent comprises a haloester.

8. The method of claim 1, wherein the aliphatic reagent comprises a halocyanide, and said transforming step comprises hydrogenating the cyanide functionality to an amine functionality.

9. The method of claim 1, wherein the ester comprises a malonate.

10. A method for making a valproic acid derivative comprising the steps of:
   (a) reacting a valproic acid precursor with an aliphatic reagent, wherein;
      (i) the valproic acid precursor consists essentially of a tertiary substituted carbon atom, the tertiary substitutions being n-propyl, $R^1$, and $R^2$, where $R^1$, and $R^2$ are ester groups, and;
      (ii) the aliphatic reagent comprises a haloester which consists essentially of an aliphatic chain between four carbons and twenty carbons in length, the aliphatic chain having the halogen attached at one end of the aliphatic chain, and the ester attached at the other end of the aliphatic chain,
   the reaction being carried out for a length of time between about 2 hours and about 4 hours at a temperature of between about 15° C. and about 25° C., and then for a length of time of between about 14 hours and about 18 hours at a temperature of between about 50° and about 70° C., thereby making an alkylated valproic acid precursor;
   (b) hydrolyzing the alkylated valproic acid precursor in a basic pH medium to obtain a carboxylated substance; transforming the alkylated valproic acid precursor into a valproic acid derivative by hydrolyzing the alkylated valproic acid precursor in a liquid medium, and;
   (c) decarboxylating the carboxylated substance in an acidic pH medium to remove a single carboxyl group and make the valproic acid derivative, and;
   (d) separating the valproic acid derivative from the acidic pH medium, the valproic acid derivative consisting essentially of a valproic acid molecule having,
      (i) an α-n-propyl group;

(ii) a carboxylic acid group; and (iii) an α-saturated aliphatic chain of at least four carbons in length, wherein the free end of the saturated aliphatic chain is attached to a carboxyl group, the saturated aliphatic chain thereby providing at least a one carbon atom extension of a δ carbon atom of the valproic acid molecule.

11. The method of claim 10 wherein the decarboxylating step is carried out for a length of time of between about 5 hours and about 15 hours.

12. A method for making a valproic acid derivative, the method comprising the steps of:

(a) reacting a valproic acid precursor with an aliphatic reagent, the valproic acid precursor consisting essentially of a tertiary substituted carbon atom, the tertiary substitutions being n-propyl, $R^1$ and $R^2$, where $R^1$ and $R^2$, are ester groups, the aliphatic reagent comprising a halocyanide, which consists essentially of an aliphatic chain between four carbons and twenty carbons in length, the aliphatic chain having the halogen attached at one end of the aliphatic chain, and the cyano group attached at the other end of the aliphatic chain, the reaction being carried out for a length of time of between about 2 hours to about 4 hours at a temperature of between about 15° to about 25° C., and then for a length of time of between about 14 hours and about 18 hours at a temperature of between about 50° and about 70° C., thereby making an alkylated valproic acid precursor;

(b) hydrogenating and acylating the alkylated valproic acid precursor to obtain an aminated compound, the hydrogenating step being carried out for between about 10 hours and about 14 hours at a pressure between about 30 PSI and about 60 PSI;

(c) hydrolyzing the aminated compound in an acidic pH medium to make the valproic acid derivative and;

(d) separating the valproic acid derivative from the acidic medium, the valproic acid derivative consisting essentially of a valproic acid molecule having, (i) an α-n-propyl group;

(ii) a carboxylic acid group; and (iii) an α-saturated aliphatic chain of at least four carbons in length, wherein the free end of the saturated aliphatic chain is attached to an amino group, the saturated aliphatic chain thereby providing at least a one carbon atom extension of a δ carbon atom of the valproic acid molecule.

13. A method for making an immunoreactive valproic acid conjugate, comprising the steps of:

(a) reacting a valproic acid precursor with an aliphatic reagent, to make an alkylated compound, said valproic acid precursor consisting essentially of a tertiary substituted carbon atom, the tertiary substitutions being n-propyl, $R^1$ and $R^2$, where $R^1$ and $R^2$, are ester groups, and said aliphatic reagent consists essentially of an aliphatic chain between four carbons and twenty carbons in length, the aliphatic chain having an inorganic, displaceable and reactive moiety at one end of the aliphatic chain, the reactive moiety being displaced during reaction with the tertiary substituted carbon atom of the valproic acid precursor carbanion intermediate, and a moiety at the other end of the aliphatic chain selected from the group consisting of cyano functionalities capable of hydrolyzing to form an amino functionality and functionalities capable of hydrolyzing to form a carboxy functionality;

(b) transforming the alkylated compound into a valproic acid derivative by hydrolyzing the alkylated compound in a liquid medium, the hydrolyzed compound having a reactive functionality selected from the group consisting of amino and carboxylate;

(c) separating the valproic acid derivative from the liquid medium, the valproic acid derivative consisting essentially of a valproic acid molecule having, (i) an α-n-propyl group;

(ii) a carboxylic acid group; and (iii) an α-saturated aliphatic chain of at least four carbons in length, wherein the free end of the saturated aliphatic chain is attached to the reactive functionality, the saturated aliphatic chain thereby providing at least a one carbon atom extension of a δ carbon atom of the valproic acid molecule;

(d) joining the saturated aliphatic chain of the valproic acid derivative to a ligand, thereby making a valproic acid preconjugate, said joining accomplished by reacting said reactive functionality with said ligand; and (f) combining the valproic acid preconjugate with a specific binding partner for the ligand, thereby making an immunoreactive valproic acid conjugate.

* * * * *